US005514136A

United States Patent [19]
Richelsoph

[11] Patent Number: 5,514,136
[45] Date of Patent: May 7, 1996

[54] SURGICAL INSTRUMENT FOR DRIVING AND ROTATING A LONG BONE PROSTHESIS

[75] Inventor: Marc E. Richelsoph, Memphis, Tenn.

[73] Assignee: Wright Medical Technology, Inc., Arlington, Tenn.

[21] Appl. No.: 300,973

[22] Filed: Sep. 6, 1994

[51] Int. Cl.⁶ .......................... A61B 17/92; A61B 17/88
[52] U.S. Cl. ................................................ 606/99; 606/86
[58] Field of Search ............................. 606/99, 100, 95, 606/86, 85

[56] References Cited

U.S. PATENT DOCUMENTS 5,064,427  11/1991  Burkinshaw ............................. 606/99

FOREIGN PATENT DOCUMENTS 2615097  11/1988  France ..................................... 606/99
2686016  7/1993  France ..................................... 606/99

*Primary Examiner*—Michael H. Thaler
*Assistant Examiner*—Scott B. Markow
*Attorney, Agent, or Firm*—Walker, McKenzie & Walker

[57] ABSTRACT

A surgical instrument for driving and rotating a prosthesis of the type having a stem for implanting into a bone, and a neck extending from the stem. The surgical instrument includes a shaft having a first end for engaging the prosthesis, having a second end, and having an axis between the first and second ends; and a bracket adjustably attached to the shaft so that the relative position between the shaft and the bracket can be adjusted, and for gripping the neck of the prosthesis so that force applied along the axis of the shaft toward the first end of the shaft will drive the prosthesis into the bone and so that rotational force applied to the axis of the shaft will rotate the prosthesis.

11 Claims, 2 Drawing Sheets

SURGICAL INSTRUMENT FOR DRIVING AND ROTATING A LONG BONE PROSTHESIS

BACKGROUND OF THE INVENTION

1. Field of the Invention

The present invention relates, in general, to an instrument for implanting a prosthesis and, more specifically, to an instrument for driving a long bone prosthesis along a longitudinal axis and for rotating the long bone prosthesis about the longitudinal axis.

2. Background Art

A long bone prosthesis, such as a femoral hip prosthesis, typically includes an elongated stem for insertion into a long bone canal; a neck attached to the proximal end of the stem; and a head attached to the proximal end of the neck for articulating with a coacting prosthesis or with natural structure. The head may be integrally attached to the neck or may be removably attached to the neck through a Morse taper or the like. The neck may be angled relative to the longitudinal axis of the stem. The angle between the neck and the longitudinal axis of the stem may vary from prosthesis to prosthesis. This is especially true for custom manufactured prostheses (i.e., prostheses manufactured based on radiographs or the like to fit specific patients).

To implant such long bone prostheses, a surgeon normally prepares the medullary canal of the long bone to receive the elongated stem of the prosthesis, and then inserts the stem into the prepared canal. The prosthesis must be properly positioned within the canal so that the articulating surface of the head will ultimately mate correctly with the articulating surface of the coacting prosthesis or natural structure, etc. It is normally necessary for the surgeon to use force to drive the prostheses into the prepared canal, especially for so-called press-fit prostheses as opposed to cemented prostheses. Simple punch-like drivers are sometimes used to seat such press-fit prostheses. Prostheses may be provided with indentations in a proximately directed surface thereof for receiving the distal ends of such punch-like drivers.

Although proper preparation of the medullary canal may guide the prosthesis to seat where the surgeon wants, a tight fit or variations in the 3-dimensional geometry may urge or rotate the prosthesis into some undesirable position. In order to insure such proper positioning, the surgeon may be required to rotate the stem within the canal, etc. In such cases, the prosthesis should be rotated or otherwise moved into the desired position with care to insure that the prosthesis is not damaged. A mere scratch on an articulating surface of the prosthesis or on the taper of the prosthesis can cause the prosthesis to be unusable.

The design, dimension and geometry of long bone prostheses vary greatly from one prosthesis to another. This is especially true for custom implants where numerous dimensions, angles, etc., of the implant are allowed to change in order to optimize implant fit for each individual patient. Not only do length, width, and geometry change, the neck angle can also change as required to restore best possible anatomic function. Such variations in design, dimension and geometry, etc., have created the need for similar variations in tools used to implant such prostheses.

Nothing in the known prior art discloses or suggests the present invention. More specifically, nothing in the known prior art discloses or suggests a surgical instrument for driving and rotating a prosthesis and including, in general, a shaft having a first end for engaging the prosthesis, having a second end, and having an axis between the first and second ends; and grip means adjustably attached to the shaft so that the relative position between the shaft and the grip means can be adjusted, and for gripping the neck of the prosthesis so that force applied along the axis of the shaft toward the first end of the shaft will drive the prosthesis into the bone and so that rotational force applied to the axis of the shaft will rotate the prosthesis.

SUMMARY OF THE INVENTION

The present invention provides an instrument for driving a prosthesis into a bone and for rotating the prosthesis within the bone. A basic concept of the present invention is to provide a surgical instrument that can be used to drive a prosthesis into a medullary canal of a long bone, and that also provides the surgeon with rotational control of the prosthesis while seating the prosthesis.

The instrument of the present invention is used in combination with a prosthesis having a stem for implanting into a bone and a neck extending from the stem. The surgical instrument of the present invention includes, in general, a shaft having a first end for engaging the prosthesis, having a second end, and having an axis between the first and second ends; and grip means adjustably attached to the shaft so that the relative position between the shaft and the grip means can be adjusted, and for gripping the neck of the prosthesis so that force applied along the axis of the shaft toward the first end of the shaft will drive the prosthesis into the bone and so that rotational force applied to the axis of the shaft will rotate the prosthesis.

One object of the present invention is to provide a surgical instrument for use in driving the stem of a prosthesis into a bone and for rotating the prosthesis within the bone.

Another object of the present invention is to provide such an instrument that will adapt to fit prostheses of different sizes, shapes and designs.

Another object of the present invention is to provide such an instrument that has the ability to adapt to any prosthesis neck length or neck angle.

Another object of the present invention is to provide such an instrument that has the ability to be easily adjusted to a fixed neck angle and neck length for use with parametrically sized hip implant sets.

Another object of the present invention is to provide such an instrument that has the ability to provide rotation control of the implant during implantation by using the implant neck to provide an off-axis structure to attach to.

Another object of the present invention is to provide such an instrument that has the ability to use an auxiliary handle to aid in rotation control.

Another object of the present invention is to provide such an instrument in which the auxiliary handle is removable and positionable on either side of the instrument.

Another object of the present invention is to provide such an instrument that can be used without portions thereof as a simple driver.

DESCRIPTION OF THE PREFERRED EMBODIMENT

Figure 1:
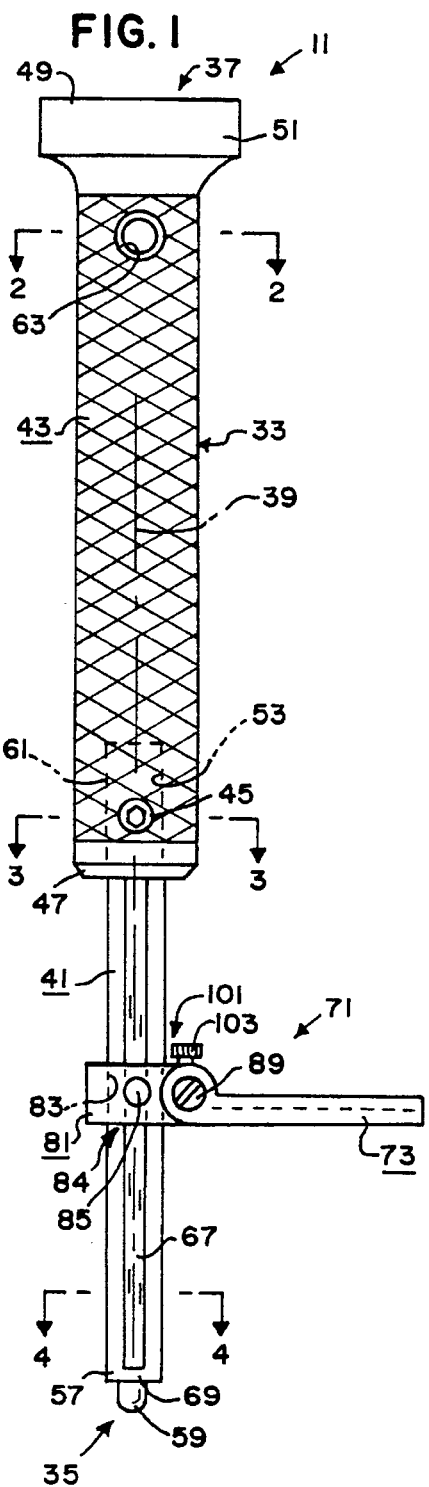
FIG. 1 is a side elevational view of a preferred embodiment of the instrument of the present invention.
Figure 2:
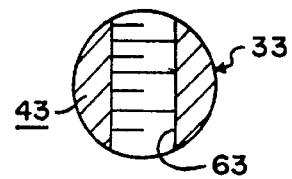
FIG. 2 is a sectional view substantially as taken on line 2—2 of FIG. 1 on an enlarged scale and with portions omitted for clarity.
Figure 3:
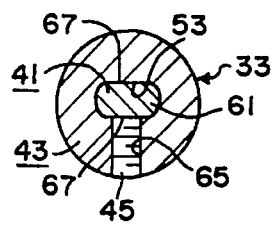
FIG. 3 is a sectional view substantially as taken on line 3—3 of FIG. 1 on an enlarged scale and with portions omitted for clarity.
Figure 4:
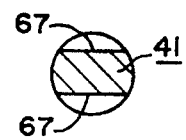
FIG. 4 is a sectional view substantially as taken on line 4—4 of FIG. 1 on an enlarged scale for clarity.

A preferred embodiment of the instrument of the present invention is shown in FIGS. 1–9, and identified by the numeral 11. The instrument 11 is for use with a long bone prosthesis such as a femoral hip prosthesis 13 (see FIGS. 8 and 9) having an elongated stem 15 for insertion into a long bone canal such as the prepared medullary canal 17 of a human femur 19, having a neck 21 extending from the upper or proximal end of the stem 15, and having a taper 23 on the upper or proximal end of the neck 21 for allowing a head (not shown) to be attached thereto as will now be apparent to those skilled in the art, or optionally having a head (not shown) permanently attached to the upper or proximal end of the neck 21. The lower or distal end of the stem 15 has a longitudinal or central axis 25. The neck 21 has a longitudinal or central axis 27. The axis 27 of the neck 21 is located at an angle relative to the axis 25 of the stem 15. This angle between the axis 27 and the axis 25 can vary from prosthesis to prosthesis depending on the design of the prosthesis, the anatomy of the patient, etc. The neck 21 typically has a first side 29 and a second side 30 with the first and second sides 29, 30 being opposed and substantially parallel to one another and being substantially flat side areas (see FIG. 9). The prosthesis 13 may have an indentation 31 or the like in a proximal portion thereof (see FIG. 8) for receiving the distal end of a typical punch-type driver (not shown). The indentation 31 is located in a position which allows access thereto from above the prosthesis 13 as the prosthesis 13 is being inserted or driven into the canal 17 and which allows force to be applied to the prosthesis 13 substantially along the axis 25 of the stem 15 as will now be apparent to those skilled in the art.

The instrument 11 of the present invention includes an elongated shaft 33 having a first end 35 for engaging the prosthesis 13, having a second end 37 and having a longitudinal axis 39 between the first and second ends 35, 37. The shaft 33 preferably includes an elongated post 41 and an elongated handle 43 for being manually held by a surgeon or the like and extending from one end of the post 41. The post 41 and handle 43 of the shaft 33 are preferably constructed separate from one another and removably joined together by a set screw 45 or the like.

The handle 43 preferably includes a first end 47 and a second end 49. The second end 49 preferably has an enlarged head 51 for allowing force to be applied thereby with hammers or the like. The first end 47 preferably has a bore 53 formed therein along the longitudinal axis 39 of the shaft 33.

The post 41 of the shaft 33 preferably includes a first end 57 having a peg-like tip 59 for extending into the indentation 31 of the prosthesis 13 to thereby make secure contact with the prosthesis 13, and having a second end 61 for extending into the bore 53 in the first end 47 of the handle 43.

Figure 8:
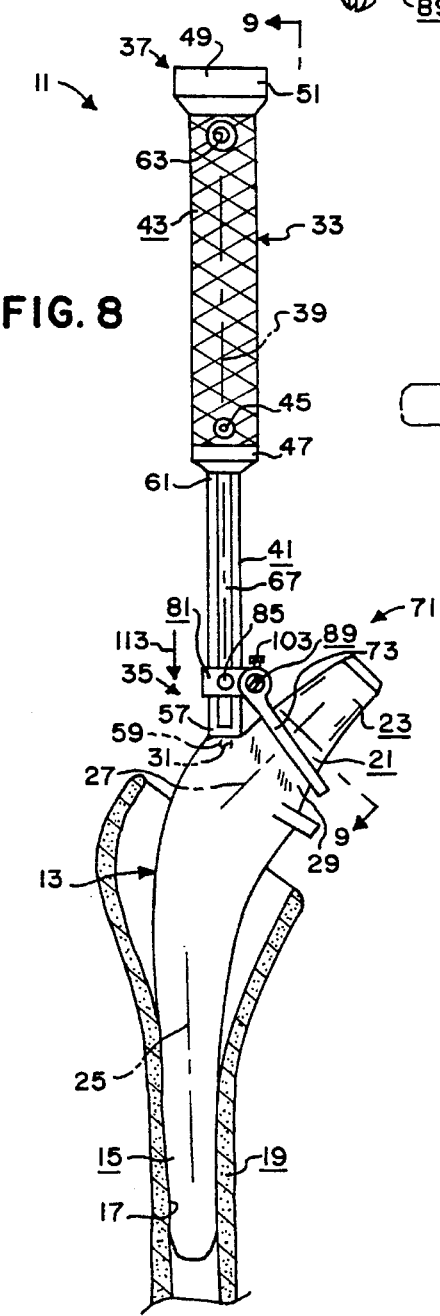
FIG. 8 is a side elevational view of the instrument of FIG. 1 shown in combination with a femoral hip prosthesis and a prepared femur.
Figure 9:
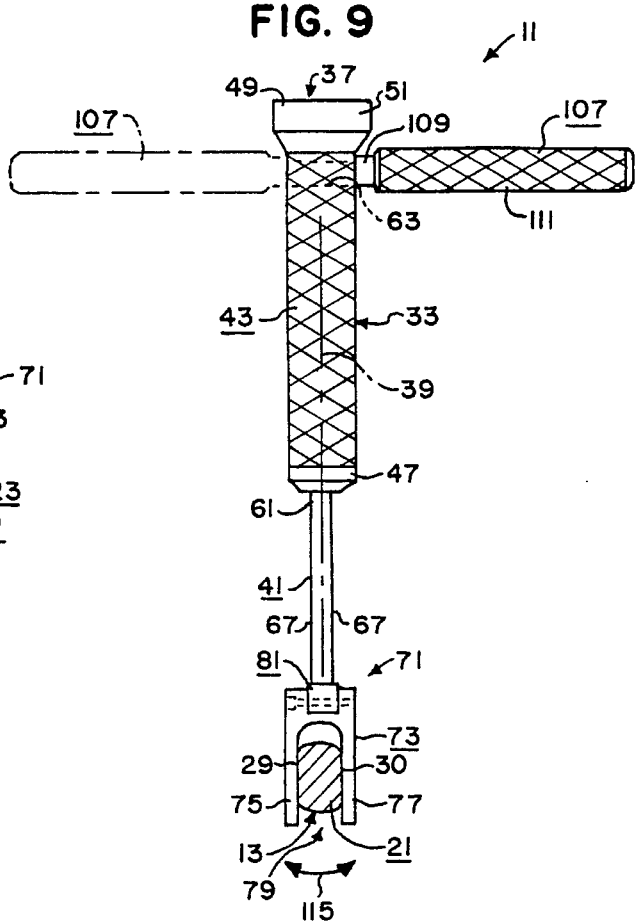
FIG. 9 is a sectional view substantially as taken on line 9—9 of FIG. 8 with portions omitted, added and shown in broken lines for clarity.

The handle 43 of the shaft 33 may be machined or otherwise constructed from stainless steel or the like with a substantial portion of the outer surface thereof knurled or otherwise designed so as to provide a secure manual grip for a surgeon or the like (see FIGS. 1, 8 and 9). The size of the handle 43 may vary. For example, for use with a typical femoral hip prosthesis 13, the handle 43 may have an overall length of approximately 6 inches (152.4 millimeters) and an outer diameter of approximately 1 inch (25.4 millimeters). An internally threaded bore 63 is preferably provided through the handle 43 adjacent the second end 49 thereof transverse to and through the longitudinal axis 39 of the shaft 33 for reasons which will become apparent. An internally threaded bore 65 preferably extends from the outer surface of the handle 43 to the bore 53 transverse to the longitudinal axis 39 of the shaft 33 for allowing the set screw 45 to secure the second end 61 of the post 41 to the first end 47 of the handle 43 (see FIG. 3).

Figure 5:
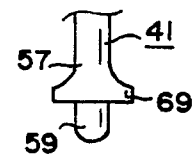
FIG. 5 is a front elevational view of the distal end of the instrument of FIG. 1 on an enlarged scale for clarity.
Figure 6:
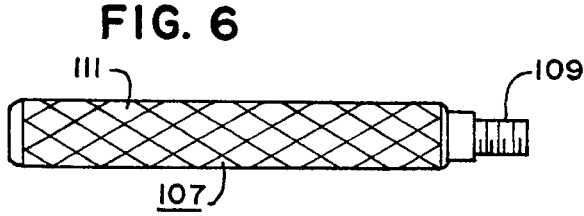
FIG. 6 is a front elevational view of a accessory grip for the instrument of FIG. 1.
Figure 7:
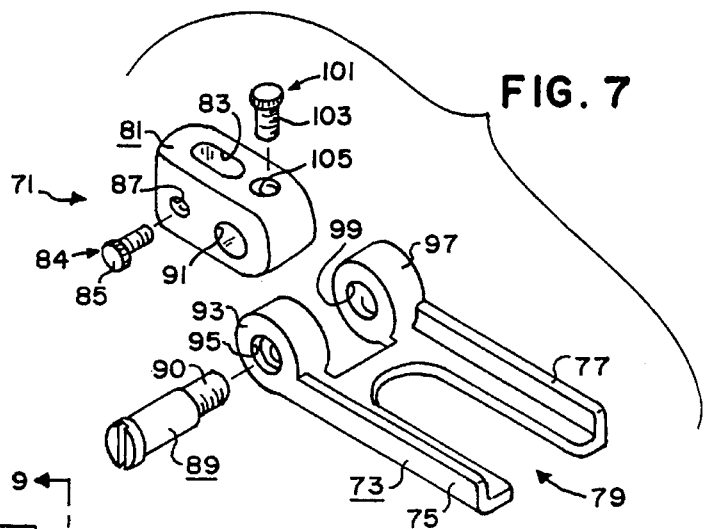
FIG. 7 is an exploded perspective view of the grip means of the instrument of FIG. 1.

The post 41 of the shaft 33 may also be machined or otherwise constructed from stainless steel or the like. The size of the post 41 may also vary. For example, for use with a typical femoral hip prosthesis 13, the post 41 may have an overall length of approximately 5 inches (127.0 millimeters) and an outer diameter of approximately 0.5 inch (12.7 millimeters). Flats 67 are preferably machined or otherwise formed on opposite sides of the post 41 along all but the extreme first end 57 thereof to form a flange 69 at the extreme first end 57 thereof (see, in general, FIG. 5) for reasons which will hereinafter become apparent. The peg-like tip 59 is shaped and sized to fit within the indentation 31 in the prosthesis 13. Thus, the peg-like tip 59 may be cylindrical with a semi-spherical outer end as shown in FIGS. 1 and 5, etc., as will now be apparent to those skilled in the art.

The instrument 11 of the present invention includes grip means 71 adjustably attached to the shaft 33 so that the relative position between the shaft 33 and the grip means 71 can be adjusted, for gripping the neck 21 of the prosthesis 13, and for rotating the prosthesis 13 about the longitudinal axis 25 of the stem 15 of the prosthesis 13 when the shaft 33 is rotated about the longitudinal axis 39 thereof.

The grip means 71 preferably includes a fork-like bracket member 73 having a first arm 75 for extending along and engaging the first side 29 of the neck 21 of the prosthesis 13 and having a second arm 77 for extending along and engaging the second side 30 of the neck 21 of the prosthesis 13 as clearly shown in FIG. 9. More specifically, the first and second arms 75, 77 coact to create a slot 79 therebetween (see FIG. 7) for receiving the neck 21 of the prosthesis 13.

The grip means 71 preferably includes a collar member 81 slidably positioned on the post 41 for connecting the bracket member 73 to the post 41. The collar member 81 has a first aperture 83 for receiving the post 41. The cross-sectional shape and size of the aperture 83 is preferably substantially the same as the cross-sectional shape and size of the portion of the post 41 having the flats 67 (i.e., all but the extreme first end 57 of the post 41 at the flange 69) so that the collar member 81 can easily slide up and down the portion of the post 41 having the flats 67 but will not rotate about the longitudinal axis of the post 41.

The grip means 71 preferably includes lock means 84 for locking the collar member 81 to the post 41 and for preventing movement of the collar member 81 on the post 41. The lock means 84 preferably includes a lock screw 85 for screwing through the collar member 81 and abutting the post 41. The collar member 81 may have a threaded aperture 87 therein communicating with the aperture 83 and the lock screw 85 may consist of a typical thumb screw or the like for screwing into the threaded aperture 87 and against the post 41 to allow the collar member 81 to be manually secured to the post 41, etc., as will now be apparent to those skilled in the art.

The grip means 71 preferably includes pivot means 89 for pivotally attaching the bracket member 73 to the collar member 81. The pivot means 89 may consist of a typical cap screw or the like. The collar member 81 preferably has an aperture 91 therethrough as clearly shown in FIG. 7 for allowing the pivot means 89 to extend therethrough. The bracket member 73 preferably includes a first ear 93 having an aperture 95 therethrough for allowing the pivot means 89 to extend therethrough, and a second ear 97 spaced from the first ear 93 a distance at least equal to the width of the collar member 81 and having a threaded aperture 99 therethrough for screwably receiving the threaded end 90 of the pivot means 89. Thus, the bracket member 73 may be pivotally attached to the collar member 81 by inserting the end of the collar member 81 between the first and second ears 93, 97 of the bracket member 73; aligning the apertures 91, 95, 99 with one another; inserting the pivot means 89 through the apertures 91 and 95; and then screwing the pivot means 89 into the threaded aperture 99.

The grip means 71 preferably includes lock means 101 for locking the bracket member 73 to the collar member 81 in a desired position and for preventing rotation of the bracket member 73 relative to the collar member 81. The lock means 101 may include a lock screw 103 or the like for locking the collar member 81 to the pivot means 89 and for preventing movement of the collar member 81 about the pivot means 89. The collar member 81 may have a threaded aperture 105 therein communicating with the aperture 91 and the lock screw 103 may consist of a typical thumb screw or the like for screwing into the threaded aperture 105 and against the pivot means 89 to allow the collar member 81 to be manually secured to the pivot means 89, etc., as will now be apparent to those skilled in the art.

The bracket member 73 of the grip means 71 may be machined or otherwise constructed from stainless steel or the like in any manner now apparent to those skilled in the art. The size of the bracket member 73 may vary. For example, for use with a typical femoral hip prosthesis 13, the slot 79 formed between the arms 75, 77 of the bracket member 73 may have an overall width of approximately 0.625 inches (15.88 millimeters) and an overall length of approximately 1.5 inches (38.1 millimeters).

The collar member 81 of the grip means 71 may be machined or otherwise constructed from stainless steel or the like in any manner now apparent to those skilled in the art. The size of the collar member 81 may vary and is substantially controlled by the size of the post 41 of the shaft 33 and the size of the bracket member 73 of the grip means 71. That is, the aperture 83 through the collar member 81 is sized and shaped to slidably receive the post 41 and the width of the collar member 81 is sized to fit between the ears 93, 97 of the bracket member 73.

The lock screw 85, pivot means 89, and lock means 101 may be off-the-shelf stainless steel components or the like.

The instrument 11 may include an auxiliary handle 107 (see FIG. 6) for being secured to the handle 43 transverse to the longitudinal axis 39 of the shaft 33 (see FIG. 9) and for allowing a surgeon to easily rotate the instrument 11 about the longitudinal axis 39 of the shaft 33. The auxiliary handle 107 preferably has an externally threaded end portion 109 for being screwed into the internally threaded bore 63 in the handle 43 of the shaft 33, and a grip portion 111 for being selectively grasped by a surgeon to rotate the shaft 33. The auxiliary handle 107 may be machined or otherwise constructed from stainless steel or the like with a substantial portion of the outer surface of the grip portion 111 thereof knurled or otherwise designed so as to provide a secure manual grip for a surgeon or the like. The size of the auxiliary handle 107 may vary. For example, for use with a typical femoral hip prosthesis 13, the auxiliary handle 107 may have an overall length of approximately 5 inches (127 millimeters) and an outer diameter of approximately 0.625 inch (15.88 millimeters). The externally threaded end portion 109 is sized to screwably coact with the internally threaded bore 63 in the handle 43.

To use the instrument 11 to implant a specific individual prosthesis 13, the instrument 11 is adjusted to fit the unique dimensions and angles of that individual prosthesis 13. That is, the collar member 81 is slid up and/or down on the post 41 and the bracket member 73 is pivoted relative to the collar member 81 until the bracket member 73 is positioned so that the arms 75, 77 thereof will extend along opposite sides 29, 30 of the neck 21 of the prosthesis 13 as clearly shown in FIG. 9 when the first end 57 of the post 41 is positioned against an appropriate portion of the prosthesis 13 (e.g., when the peg-like tip 59 of the first end 57 of the post 41 is inserted into the indentation 31 in the prosthesis 13 as clearly shown in FIG. 8) and the longitudinal axis 39 of the shaft 33 substantially aligned with the longitudinal axis 25 of the stem 15 of the prosthesis 13 as shown in FIG. 8. The lock screws 85, 103 can be loosened to allow easy adjustment of the collar member 81 and bracket member 73, and can be tightened to lock the collar member 81 and bracket member 73 in position as will now be apparent to those skilled in the art. Care should be taken to properly adjust the collar member 81 and bracket member 73 to insure that the bracket member 73 will not engage the taper 23 of the prosthesis 13 or an articulating surface (not shown) of the prosthesis 13, etc., when used to prevent scratching or other damage to such portions of the prosthesis 13. When the instrument 11 thus adjusted and positioned on the prosthesis 13 (i.e., with the peg-like tip 59 inserted into the indentation 31 and with the arms 75, 77 extending along the opposite sides 29, 30), force can be applied to the handle 43 of the shaft 33 parallel to the longitudinal axis 39 of the shaft 33 to thereby force the stem 15 of the prosthesis 13 into the prepared medullary canal 17 in the direction of the arrow 113 in FIG. 8. Rotational force can also be applied to the handle 43 about the longitudinal axis 39 of the shaft 33 to thereby cause the prosthesis 13 to rotate relative to the canal 17, etc., in the direction of the arrow 115 in FIG. 9, as will now be apparent to those skilled in the art.

As thus constructed and used, the present invention provides a universal instrument that has the ability to adapt to properly fit prostheses having varying neck lengths and/or neck angles; that provides rotational control of the prosthesis during implantation by using the neck of the prosthesis to provide an off-axis structure to attach to; and that can be used as a simple driver with or without such rotational control.

Although the present invention has been described and illustrated with respect to a preferred embodiment and a preferred use therefor, it is not to be so limited since modifications and changes can be made therein which are within the full intended scope of the invention.

I claim:

1. A surgical instrument for driving and rotating a prosthesis of the type having a stem for implanting into a bone, and a neck extending from the stem; said surgical instrument comprising:

(a) a shaft having a first end for engaging said prosthesis, having a second end, and having an axis between said first and second ends; and (b) grip means adjustably attached to said shaft so that the relative position between shaft and said grip means can be adjusted, and for gripping said neck of said prosthesis so that force applied along said axis of said shaft toward said first end of said shaft will drive said prosthesis into said bone and so that rotational force applied to said axis of said shaft will rotate said prosthesis; said grip means including first and second arms, each of said arms having a first end attached relative to said shaft and a second end remote from said shaft, said second ends of said arms are spaced apart from one another to define an opening for receiving said neck of said shaft.

2. A surgical instrument for driving and rotating a prosthesis of the type having a stem for implanting into a bone, and a neck extending from the stem; said surgical instrument comprising:

(a) a shaft having a first end for engaging said prosthesis, having a second end, and having a longitudinal axis between said first and second ends;

(b) grip means slidably attached to said shaft for sliding between said first and second ends of said shaft so that the distance between said first end of said shaft and said grip means can be adjusted, and for gripping said neck of said prosthesis so that force applied along said axis of said shaft toward said first end of said shaft will drive said prosthesis into said bone and so that rotational force applied to said axis of said shaft will rotate said prosthesis;

(c) pivot means attaching said grip means to said shaft for allowing pivotal movement of said grip means about a axis substantially perpendicular to said longitudinal axis of said shaft: and (d) lock means for selectively preventing pivotal movement of said grip means about the axis substantially perpendicular to said longitudinal axis of said shaft.

3. The surgical instrument of claim 2 in which said neck of said prosthesis has a first side and a second side; and in which said grip means includes a bracket member having a first arm for engaging said first side of said neck of said prosthesis and having a second arm for engaging said second side of said neck of said prosthesis; each of said arms having a first end attached relative to said shaft and a second end remote from said shaft, said second ends of said arms are spaced apart from one another to define an opening for receiving said neck of said shaft.

4. The surgical instrument of claim 3 in which said grip means includes a collar member slidably positioned on said shaft for connecting said bracket member to said shaft, said collar member having an aperture therethrough for slidably receiving said shaft.

5. A surgical instrument for driving and rotating a prosthesis of the type having a stem for implanting into a bone, and a neck extending from the stem; said neck of said prosthesis having a first side and a second side; said surgical instrument comprising:

(a) a shaft having a first end for engaging said prosthesis, having a second end, and having an axis between said first and second ends; and (b) grip means slidably attached to said shaft for sliding between said first and second ends of said shaft so that the distance between said first end of said shaft and said grip means can be adjusted, and for gripping said neck of said prosthesis so that force applied along said axis of said shaft toward said first end of said shaft will drive said prosthesis into said bone and so that rotational force applied to said axis of said shaft will rotate said prosthesis; said grip means including a bracket member having a first arm for engaging said first side of said neck of said prosthesis and having a second arm for engaging said second side of said neck of said prosthesis; said grip means including a collar member slidably positioned on said shaft for connecting said bracket member to said shaft, said collar member having an aperture therethrough for slidably receiving said shaft; said grip means including pivot means for pivotally attaching said bracket member to said collar member; said grip means including first lock means for locking said collar member to said shaft and for preventing movement of said collar member on said shaft, and including second lock means for locking said bracket member to said collar member and for preventing pivotal movement of said bracket member relative to said collar member.

6. The surgical instrument of claim 5 in which said second lock means locks said bracket member, said collar member and said pivot means together to prevent pivotal movement of said bracket member relative to said collar member.

7. The surgical instrument of claim 2 in which said prosthesis has an indentation therein; and in which said shaft includes an elongated post having a first end with a peg-like member for extending into said indentation of said prosthesis, and having a second end; in which said shaft includes a handle having a first end for being attached to said second end of said post, and having a second end.

8. The surgical instrument of claim 7 in which is included an auxiliary handle for being secured to said handle of said shaft transverse to said longitudinal axis of said shaft.

9. A surgical instrument for driving and rotating a prosthesis of the type having a stem for implanting into a bone, and a neck extending from the stem; said neck of said prosthesis having a first side and a second side; said surgical instrument comprising:

(a) a shaft having a first end for engaging said prosthesis, having a second end, and having an axis between said first and second ends; and (b) grip means pivotally attached to said shaft so that the angle between said shaft and said grip means can be adjusted, and for gripping said neck of said prosthesis so that force applied along said axis of said shaft toward said first end of said shaft will drive said prosthesis into said bone and so that rotational force applied to said axis of said shaft will rotate said prosthesis; said grip means including a bracket member having a first arm for engaging said first side of said neck of said prosthesis and having a second arm for engaging said second side of said neck of said prosthesis; said grip means including a collar member slidably positioned on said shaft for connecting said bracket member to said shaft, said collar member having an aperture therethrough for slidably receiving said shaft; said grip means including pivot means for pivotally attaching said bracket member to said collar member; said grip means including first lock means for locking said collar member to said shaft and for preventing movement of said collar member on said, and including second lock means for locking said bracket member to said collar member and for preventing pivotal movement of said bracket member relative to said collar member.

10. The surgical instrument of claim 9 in which said second lock means locks said bracket member, said collar member and said pivot means together to prevent pivotal movement of said bracket member relative to said collar member.

11. A surgical instrument for a prosthesis of the type having a stem for implanting into a bone, and a neck extending from the stem; said neck of said prosthesis having a first side and a second side; said surgical instrument comprising:

(a) a shaft having a first end, a second end, and an axis between said first and second ends; and (b) a grip slidably and pivotally attached to said shaft; said grip including a bracket member having an open ended slot defined by spaced apart first and second arms spaced apart from one another a distance at least equal to the distance between said first and second sides of said neck of said prosthesis; said grip including a collar member slidably positioned on said shaft connecting said bracket member to said shaft, said collar member having an aperture therethrough slidably receiving said shaft; said grip including a pivot pivotally attaching said bracket member to said collar member; said grip including a first lock locking said collar member to said shaft and preventing movement of said collar member on said shaft, and including a second lock locking said bracket member to said collar member.

* * * * *